United States Patent
Kadykowski

(10) Patent No.: US 9,173,718 B2
(45) Date of Patent: Nov. 3, 2015

(54) BLOOD VESSEL MARKING SYSTEM

(71) Applicant: Terumo Cardiovascular Systems Corporation, Ann Arbor, MI (US)

(72) Inventor: Randal J. Kadykowski, South Lyon, MI (US)

(73) Assignee: Terumo Cardiovascular Systems Corporation, Ann Arbor, MI (US)

( * ) Notice: Subject to any disclaimer, the term of this patent is extended or adjusted under 35 U.S.C. 154(b) by 230 days.

(21) Appl. No.: 13/851,376

(22) Filed: Mar. 27, 2013

(65) Prior Publication Data

US 2014/0296622 A1 Oct. 2, 2014

(51) Int. Cl.
*A61F 2/06* (2013.01)
*A61B 19/00* (2006.01)

(52) U.S. Cl.
CPC ............ *A61B 19/54* (2013.01); *A61F 2/062* (2013.01); *A61F 2/064* (2013.01)

(58) Field of Classification Search
CPC .................................. A61F 2/06–2/064; A61F 2250/0097–2250/0098; A61B 2019/5437; A61B 2019/545; A61B 19/54; A61L 27/507; B41N 1/24–1/248
See application file for complete search history.

(56) References Cited

U.S. PATENT DOCUMENTS

| | | | |
|---|---|---|---|
| 4,232,659 A | 11/1980 | Dale | |
| 4,944,737 A | 7/1990 | Bloom | |
| 5,496,304 A | 3/1996 | Chasan | |
| 5,662,705 A * | 9/1997 | Love et al. | 128/898 |
| 6,197,034 B1 | 3/2001 | Gvozdic et al. | |
| 6,649,030 B1 * | 11/2003 | Tesar | 204/192.14 |
| 6,869,437 B1 * | 3/2005 | Hausen et al. | 606/153 |
| 8,123,672 B2 | 2/2012 | Viitala et al. | |
| 8,900,652 B1 * | 12/2014 | Caballero et al. | 427/2.3 |
| 2004/0253281 A1 * | 12/2004 | Herweck et al. | 424/401 |
| 2007/0293932 A1 * | 12/2007 | Zilla et al. | 623/1.11 |
| 2008/0027272 A1 | 1/2008 | Kadykowski | |

FOREIGN PATENT DOCUMENTS

| | | |
|---|---|---|
| WO | 9829146 | 7/1998 |
| WO | 2013144208 A1 | 10/2013 |

* cited by examiner

*Primary Examiner* — Catherine B Kuhlman
(74) *Attorney, Agent, or Firm* — Gael Diane Tisack; Darryl Newell; MacMillan, Sobanski & Todd LLC

(57) ABSTRACT

Apparatus for marking a blood vessel for use as a bypass graft in a patient includes a preparation plate for supporting an isolated blood vessel that is in a state for anastomosing to the patient. A stencil plate is configured for overlying the blood vessel and preparation plate, wherein the stencil plate has an opening adapted to expose a portion of the blood vessel to a dye applied through the opening. The stencil plate around the opening is adapted to shield the blood vessel from the dye. A dye applicator is configured to direct a metered amount of the dye through the opening and onto the exposed portion of the blood vessel, preferably as a mist. Preferably, the opening is a lineal slot for creating a guide line extending longitudinally along an outer wall of the blood vessel.

19 Claims, 3 Drawing Sheets

BLOOD VESSEL MARKING SYSTEM

CROSS REFERENCE TO RELATED APPLICATIONS

Not Applicable.

STATEMENT REGARDING FEDERALLY SPONSORED RESEARCH

Not Applicable.

BACKGROUND OF THE INVENTION

The present invention relates in general to marking a blood vessel harvested from a patient for use in cardiac bypass graft surgery, and, more specifically, to a system for applying predetermined reference marking on the blood vessel to assist in surgical placement.

In coronary artery bypass grafting (CABG), a blood vessel or vessel section, such as an artery or vein, is "harvested" (i.e., removed) from its natural location in a patient's body for use elsewhere in the body. In CABG surgery, the blood vessel is used to form a bypass between an arterial blood source and the coronary artery that is to be bypassed. Among the preferred sources for the vessel to be used as the bypass graft are the saphenous veins in the legs and the radial artery in the arms.

Endoscopic surgical procedures for harvesting a section of a vein (e.g., the saphenous vein) subcutaneously have been developed in order to avoid disadvantages and potential complications of harvesting through a continuous incision (e.g., along the leg) for the full length of the desired vein section in order to provide adequate exposure for visualizing the vein and for introducing surgical instruments to sever, cauterize and ligate the tissue and side branches of the vein. One such minimally-invasive technique employs a small incision for locating the desired vein and for introducing one or more endoscopic harvesting devices. Primary dissection occurs by introduction of a dissecting instrument through the incision to create a working space and separate the vein from the surrounding tissue. Then a cutting instrument is introduced into the working space to sever the blood vessel from the connective tissue surrounding the section to be harvested and any side branches of the blood vessel. The branches may be clipped and/or cauterized.

In one typical procedure, the endoscopic entry site is located near the midpoint of the vessel being harvested, with dissection and cutting of branches proceeding in both directions along the vessel from the entry site. In order to remove the desired section of the blood vessel, a second small incision, or stab wound, is made at one end thereof and the blood vessel section is ligated. A third small incision is made at the other end of the blood vessel section which is then ligated, thereby allowing the desired section to be completely removed through the first incision. Alternatively, only the first two incisions may be necessary if the length of the endoscopic device is sufficient to obtain the desired length of the blood vessel while working in only one direction along the vessel from the entry point.

An example of a commercially available product for performing the endoscopic vein harvesting described above is the VirtuoSaph™ Endoscopic Vein Harvesting System from Terumo Cardiovascular Systems Corporation of Ann Arbor, Mich. Endoscopic vein harvesting systems are also shown in U.S. Pat. No. 6,660,016 to Lindsay and U.S. Pat. No. 7,331,971 to Kasahara et al, both of which are incorporated herein by reference in their entirety.

After a vein is removed from the patient's body, it must be prepared for use as a bypass graft. Preparation includes ligating (i.e., closing off) each branch stub, injecting a solution into the vein under pressure to test for leaks, and otherwise inspecting the condition of the blood vessel. A device for assisting with this initial vessel preparation is shown in U.S. Pat. No. 8,123,672, which is hereby incorporated by reference. After preparation, the vessel can be surgically anastomosed to create the bypass.

It has become common for vessel preparation to include application of a longitudinal guide line along the outer wall of the graft comprised of a methylene blue dye. The line is intended to help in laying out the graft by showing if the graft becomes twisted, which could cause kinking and poor blood flow through the bypass. To apply the guide line, a surgeon or physician's assistant has manually marked the vessel using a pen filled with the methylene blue dye. However, the direct manipulation of the vessel can lead to harsh rubbing of the pen against the vessel, which may result in damage to the endothelium. Furthermore, the line may often be smudged and can be applied inaccurately.

SUMMARY OF THE INVENTION

The present invention provides a vessel marking system that can significantly reduce handling/touching of a blood vessel during preparation. Rubbing and abrasion can be completely eliminated while simultaneously improving the quality of the applied guide line.

In one aspect of the invention, apparatus is provided for marking a blood vessel for use as a bypass graft in a patient. A preparation plate is provided for supporting an isolated blood vessel that is in a state prepared for anastomosing to the patient. A stencil plate is configured for overlying the blood vessel and preparation plate, wherein the stencil plate has an opening adapted to expose a portion of the blood vessel to a dye applied through the opening. The stencil plate around the opening is adapted to shield the blood vessel from the dye. A dye applicator is configured to direct a metered amount of the dye through the opening and onto the exposed portion of the blood vessel.

Figure 1:
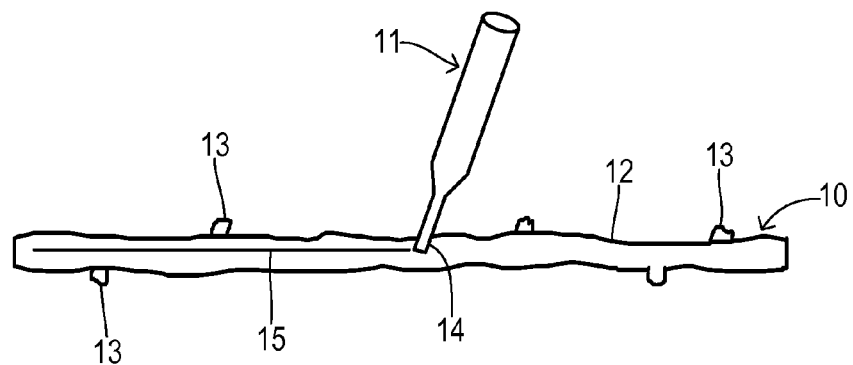
FIG. 1 shows a dye pen making a manual freehand guide line on a dissected blood vessel.

DETAILED DESCRIPTION OF PREFERRED EMBODIMENTS is Referring now to FIG. 1, a blood vessel 10 such as a saphenous vein is shown being marked by a pen 11 to apply a guide line 15 to assist a surgeon during anastomosis to a patient to avoid twisting of blood vessel 10 in its final position. Before applying a guide line 15 to outer wall 12 of blood vessel 10, preparatory steps are performed of dissecting blood vessel 10 from the patient, ligating the side branches 13, and pressure testing to ensure there are no leaks in order to bring blood vessel 10 into a state of preparedness for anastomosing onto the patient. In the prior art, blood vessel 10 has been held in one hand with a dye pen 11 held in the other hand so that a tip 14 of pen 11 is rubbed against outer wall 12 to dispense dye (such as methylene blue dye) onto blood vessel 10. The prior art application method frequently resulted in harsh treatment of the blood vessel causing damage to the endothelium. The accuracy of a guide line was hard to control and the resulting line of dye was easily smudged.

Figure 2:
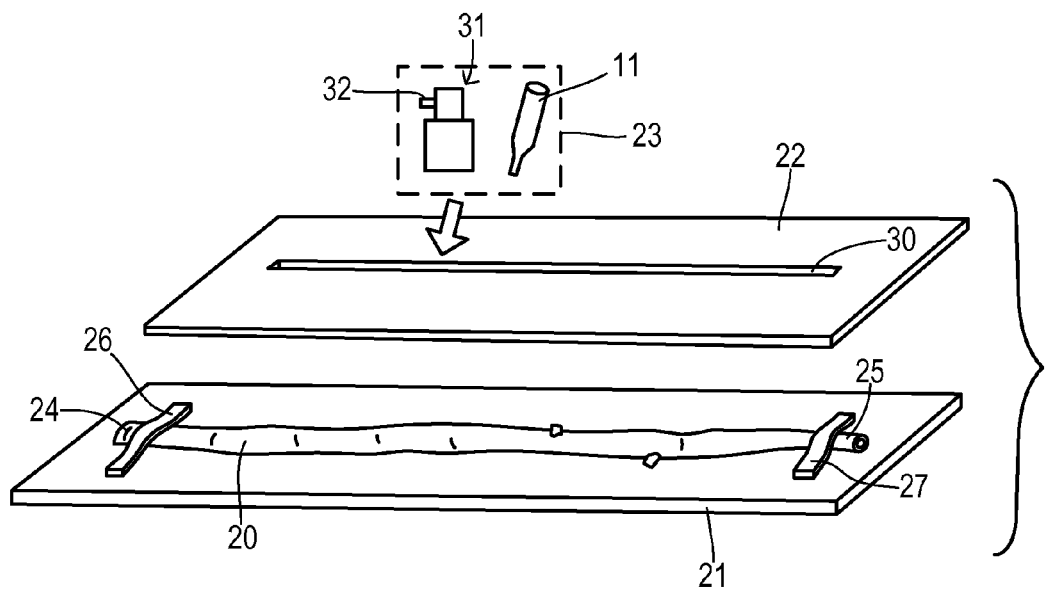
FIG. 2 is a perspective view of one embodiment of a stencil system according to the present invention.

FIG. 2 shows an improved apparatus and technique for marking a blood vessel 20 with a guide line. The apparatus includes a preparation plate 21, a stencil plate 22, and a dye applicator 23. Plates 21 and 22 may preferably be comprised of substantially flat sheets of a biocompatible, sterilizable plastic. Vessel 20 is supported on a top surface of preparation plate 21 with its ends 24 and 25 at opposite ends of plate 21 so that blood vessel 20 extends along a straight line. Ends 24 and 25 may optionally be releasably mounted to plate 21 so that blood vessel 20 does not move during the marking procedure. Strips of biocompatible tape 26 and 27 can be employed for mounting blood vessel 20.

Stencil plate 22 has an opening 30 completely penetrating to both sides of plate 22 to form a stencil to place a corresponding marking shape on blood vessel 20. Opening 30 is preferably formed as a lineal slot with a side-to-side width which is less than a minimum outside diameter of blood vessel 20 that is to be marked. Stencil plate 22 is laid upon blood vessel 20 and preparation plate 21 so that it overlies blood vessel 20 with opening 30 exposing a lineal portion of blood vessel 20 that is to be marked. Dye applicator 23 applies the marking dye through opening 30, resulting in the desired guide line and/or other markings. Although a pen can be used to apply the dye through opening 30, the dye is more preferably applied using a mister 31 having a nozzle 32 for dispensing the dye as a mist directed toward opening 30. The mist results in the formation of the guide line on blood vessel 20 without applicator 23 actually contacting blood vessel 20. Mister 31 may be comprised of any known type of device, such as a dye reservoir and a finger-activated pump for directing dye through nozzle 32 so as to aerosolize the dye into a metered amount of a mist. Any desired type of biocompatible dye can be employed, such as methylene blue dye.

Figure 3:
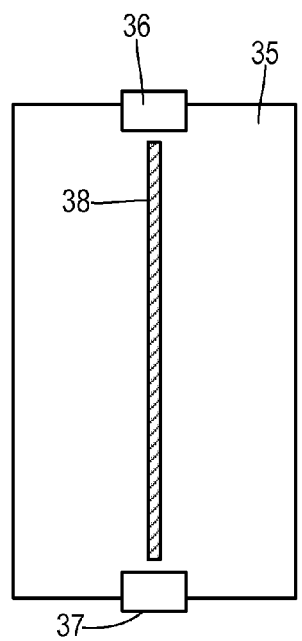
FIG. 3 is a top view of an alternative embodiment of a preparation plate.
Figure 4:
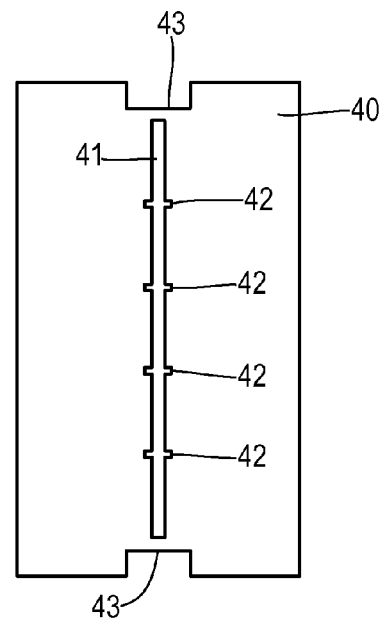
FIG. 4 is a top view of an alternative embodiment of a stencil plate.

FIG. 3 shows a plan view of another embodiment of a preparation plate 35 including clips 36 and 37 at opposite longitudinal ends for selectably and releasably mounting opposite ends of a blood vessel. Clips 36 and 37 can include a spring-loaded gripper or a plastic living hinge, for example. A placement guide marker 38 is provided on plate 35 at a position corresponding to the location of a stencil opening when a stencil plate 40 as shown in FIG. 4 is registered at a reference position atop preparation plate 35. Marker 38 assists the user in visualizing the expected placement of a guide line on a blood vessel as soon as it is laid upon preparation plate 35. Marker 38 may be comprised of a contrasting color, a surface treatment of plate 35, or a groove or depression into the surface that may be molded or etched into plate 35. Stencil plate 40 has a slot 41 extending longitudinally to create the desired guide line. Other markings or shapes may also be provided by stencil plate 40, such as widened index marks 42 that may be used to indicate a reference distance in order to help a surgeon identify a desired length of the blood vessel. A pair of notches 43 is provided for receiving clips 36 and 37 on preparation plate 35 in a manner that registers slot 41 over guide marker 38.

Figure 5:
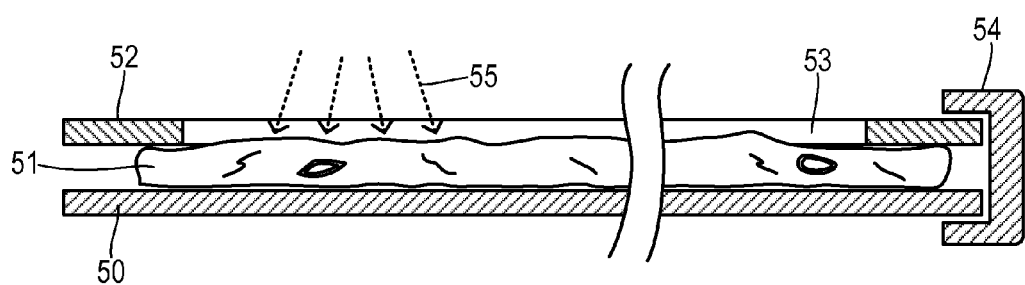
FIG. 5 is a side cross section view of a blood vessel mounted between the preparation plate and stencil plate being marked by a dye mist.

FIG. 5 is a side cross-sectional view of a marking system taken longitudinally along a marking slot of the stencil during the marking of a blood vessel. Thus, a preparation plate 50 has a prepared blood vessel 51 supported on its upper surface. A stencil plate 52 has a slot opening 53 exposing a portion of blood vessel 51. A clip or band 54 may be provided for retaining plates 50 and 52 together around blood vessel 51. This will help ensure that no relative movement occurs during the is marking process. A dye mist 55 is applied to the exposed portion of blood vessel 51 through slot opening 53, thereby providing the desired guide line on blood vessel 51 without any significant contacting of blood vessel 51 and without smudging or any inaccuracies in the layout of the guide line. If desired, the dye could be applied through slot opening 53 using a marking pen. Results with a pen would still be better than the prior art since stencil plate 52 can be gently placed over blood vessel 51 so that the majority of the blood vessel surface is protected from any mechanical damage.

Figure 6:
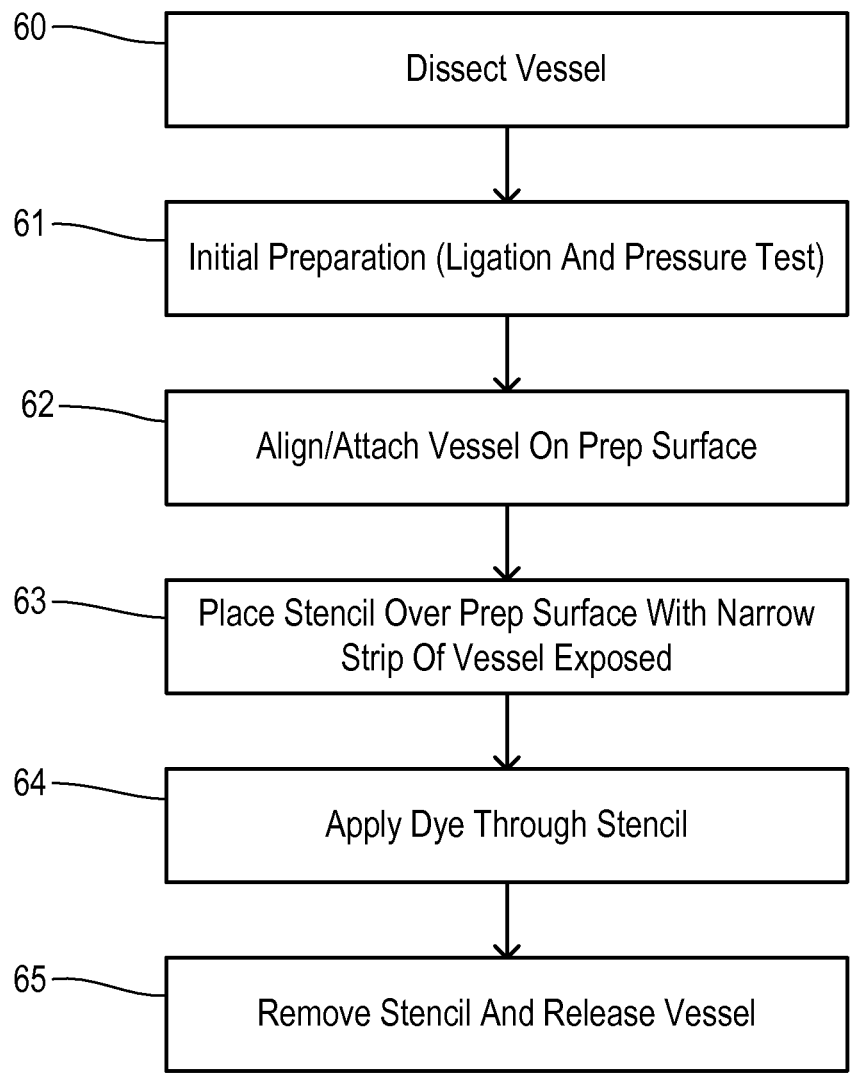
FIG. 6 is a flowchart showing one preferred method of the invention.

A method of the invention is shown in FIG. 6. A blood vessel is dissected from a patient in step 60. In step 61, an initial preparation of the blood vessel is performed including ligation of side branches and pressure testing of the blood vessel to ensure no leaks are present. Once in the state prepared for anastomosing to the patient, the blood vessel is aligned/attached onto the surface of the preparation plate in step 62. In step 63, the stencil plate is placed over the preparation plate and the blood vessel so that a narrow strip of the blood vessel is exposed through the opening in the stencil plate.

A dye such as methylene blue dye is applied through the opening in the stencil plate in step 64. Whether applied as a mist or via a marking pen, the dye application results in formation of a straight, crisp, thin guide line while causing little or no damage to the endothelium of the blood vessel. In step 65, the blood vessel is separated from the stencil plate and the preparation plate by removing the stencil and releasing the blood vessel from the preparation plate. The stencil and preparation plates may preferably be made from a disposable plastic so that they can be simply discarded after use.

What is claimed is:

1. A method of marking a blood vessel for use as a bypass graft in a patient, comprising the steps of:
isolating the blood vessel in a state prepared for anastomosing to the patient;
supporting the blood vessel on a preparation plate, wherein the preparation plate includes a placement guide marker;
laying a stencil plate over the blood vessel and preparation plate, wherein the stencil plate has an opening exposing a portion of the blood vessel, wherein the opening in the stencil plate is comprised of a substantially lineal slot having a side-to-side width less than a minimum outside diameter of a section of the blood vessel that includes the exposed portion, and wherein the preparation plate and stencil plate include registration features so that when the stencil plate is placed on the preparation plate then the placement guide marker is registered at a position corresponding to the lineal slot;
applying a dye through the opening onto the exposed portion of the blood vessel, wherein the stencil plate around the opening shields the blood vessel from the dye; and
separating the blood vessel from the stencil plate and the preparation plate, whereby the dyed portion of the blood vessel guides anastomosing the blood vessel as a bypass graft.

2. The method of claim 1 wherein the supporting step is comprised of releasably mounting the blood vessel on an upper surface of the preparation plate.

3. The method of claim 2 wherein the upper surface is substantially planar.

4. The method of claim 1 wherein the preparation plate is comprised of a substantially flat sheet of a biocompatible plastic.

5. The method of claim 1 wherein the stencil plate is comprised of a substantially flat sheet of a biocompatible plastic.

6. The method of claim 1 wherein the step of applying a dye is comprised of spraying a mist of the dye into the opening.

7. The method of claim 1 wherein the dye is comprised of methylene blue dye.

8. Apparatus for marking a blood vessel for use as a bypass graft in a patient, comprising:
   a biocompatible preparation plate for supporting an isolated blood vessel harvested from the patient that is in a state prepared for anastomosing to the patient; and
   a biocompatible stencil plate for overlying the blood vessel and preparation plate, wherein the stencil plate has an opening adapted to expose a portion of the blood vessel to a dye applied through the opening, wherein the stencil plate around the opening is adapted to shield a covered portion of the blood vessel from the dye, wherein the opening in the stencil plate is comprised of a substantially lineal slot having a side-to-side width less than a minimum outside diameter of a section of the blood vessel that includes the exposed portion;
   wherein the preparation plate includes a placement guide marker, and wherein the preparation plate and stencil plate include registration features so that when the stencil plate is placed on the preparation plate then the placement guide marker is registered at a position corresponding to the lineal slot.

9. The apparatus of claim 8 further comprising:
   a dye applicator for directing a metered amount of the dye through the opening and onto the exposed portion of the blood vessel.

10. The apparatus of claim 9 wherein the dye applicator is a mister and the metered amount of dye is applied as a mist.

11. The apparatus of claim 9 wherein the dye applicator is a pen.

12. The apparatus of claim 8 wherein the preparation plate includes a holder for retaining the blood vessel on a substantially planar upper surface of the preparation plate.

13. The apparatus of claim 12 wherein the holder is comprised of a clip.

14. The apparatus of claim 12 wherein the holder is comprised of tape.

15. The apparatus of claim 8 wherein the preparation plate is comprised of a sheet of biocompatible plastic.

16. The apparatus of claim 8 wherein the stencil plate is comprised of a sheet of biocompatible plastic.

17. The apparatus of claim 8 wherein the placement guide marker is comprised of a groove.

18. The apparatus of claim 8 wherein the placement guide marker is comprised of a contrasting color.

19. The apparatus of claim 8 wherein the opening in the stencil plate further includes widened index marks.

* * * * *